United States Patent
Norton et al.

(10) Patent No.: US 7,099,081 B2
(45) Date of Patent: Aug. 29, 2006

(54) SMALL-SPOT SPECTROMETRY INSTRUMENT WITH REDUCED POLARIZATION AND MULTIPLE-ELEMENT DEPOLARIZER THEREFOR

(75) Inventors: Adam E. Norton, Palo Alto, CA (US); Kenneth C. Johnson, Santa Clara, CA (US); Fred E. Stanke, Cupertino, CA (US)

(73) Assignee: Tokyo Electron Limited, Tokyo (JP)

( * ) Notice: Subject to any disclaimer, the term of this patent is extended or adjusted under 35 U.S.C. 154(b) by 283 days.

(21) Appl. No.: 10/081,078

(22) Filed: Feb. 21, 2002

(65) Prior Publication Data
US 2002/0126277 A1    Sep. 12, 2002

Related U.S. Application Data

(63) Continuation-in-part of application No. 09/932,548, filed on Aug. 17, 2001, now Pat. No. 6,667,805.

(60) Provisional application No. 60/350,823, filed on Jan. 18, 2002, provisional application No. 60/226,396, filed on Aug. 18, 2000.

(51) Int. Cl.
    *G02B 5/30*    (2006.01)
    *G02B 27/28*   (2006.01)
(52) U.S. Cl. ................. 359/497; 359/494; 359/499
(58) Field of Classification Search ............... 359/259, 359/497, 483, 485, 488, 494, 499, 496; 356/350, 356/326
See application file for complete search history.

(56) References Cited

U.S. PATENT DOCUMENTS

| | | | |
|---|---|---|---|
| 4,129,357 A * | 12/1978 | Frosch et al. ............... 359/497 |
| 4,269,481 A * | 5/1981 | Yeh et al. .................... 359/259 |
| 4,572,608 A | 2/1986 | Mochizuki et al. ...... 350/96.15 |
| 4,712,912 A | 12/1987 | Messerschmidt ............. 356/73 |
| 4,818,169 A | 4/1989 | Schram et al. ......... 414/331.18 |
| 4,922,309 A | 5/1990 | Sekiwa et al. ............... 356/300 |
| 5,218,652 A | 6/1993 | Lutz ............................. 385/11 |
| 5,243,465 A | 9/1993 | Fein ............................. 359/636 |
| 5,371,595 A | 12/1994 | Nishiura et al. ............. 356/350 |
| 5,430,795 A | 7/1995 | Taga et al. ................... 359/179 |
| 5,432,637 A * | 7/1995 | Hakimi ........................ 359/497 |
| 5,657,121 A | 8/1997 | Nishina ....................... 356/327 |
| 5,933,555 A | 8/1999 | Shen ............................. 385/32 |
| 6,040,906 A | 3/2000 | Harhay ........................ 356/301 |
| 6,075,646 A | 6/2000 | Suzuki ......................... 359/434 |

FOREIGN PATENT DOCUMENTS

| | | |
|---|---|---|
| EP | 0 665 452 A1 | 1/1995 |
| JP | 1-287528 | 11/1989 |
| JP | 4-358115 | 12/1992 |
| JP | 05257066 A | 10/1993 |

OTHER PUBLICATIONS

Optics. Hecht and Zajac, (Addison-Wesley Publishing Company Feb. 1979, pp. 246-249).*
M.E. Lee et al., "Analysis of Reflectometry and Ellipsometry Data from Patterned Structures", Dept. of Electrical Engineering and Computer Science, Univ. of Michigan, MI, 5 pages.

(Continued)

*Primary Examiner*—Audrey Chang
(74) *Attorney, Agent, or Firm*—Stallman & Pollock LLP (57) ABSTRACT

A small-spot imaging, spectrometry instrument for measuring properties of a sample has a polarization-scrambling element, such as a birefringent plate depolarizer, incorporated between the polarization-introducing components of the system, such as the beamsplitter, and the microscope objective of the system. The plate depolarizer varies polarization with wavelength, and may be a Lyot depolarizer with two plates, or a depolarizer with more than two plates (such as a three-plate depolarizer). Sinusoidal perturbation in the resulting measured spectrum can be removed by data processing techniques or, if the depolarizer is thick or highly birefringent, the perturbation may be narrower than the wavelength resolution of the instrument.

7 Claims, 5 Drawing Sheets

OTHER PUBLICATIONS

Nasa Research Announcement, "Technical Details on OMI and Other EOS Chem Instruments", Sep. 29, 1999, 2 pages.

Varian Inc. paper, Scientific Instruments, "Polarizer and Depolarizer Accesory", Jun. 28, 2000, 2 pages.

* cited by examiner

SMALL-SPOT SPECTROMETRY INSTRUMENT WITH REDUCED POLARIZATION AND MULTIPLE-ELEMENT DEPOLARIZER THEREFOR

CROSS-REFERENCE TO RELATED APPLICATIONS

This application is a continuation-in-part of U.S. patent application Ser. No. 09/932,548, filed Aug. 17, 2001, which claims priority under 35 U.S.C. 119(e) from prior U.S. provisional application No. 60/226,396, filed Aug. 18, 2000. This application also claims priority under 35 U.S.C. 119(e) from U.S. provisional application No. 60/350,823, filed Jan. 18, 2002.

TECHNICAL FIELD

The present invention relates generally to optical metrology systems that measure optical characteristics of a sample in order to determine physical properties of interest of the sample. Systems having optical instruments that measure light scattered from a sample (whether by reflection or transmission) and which interpret the measured characteristics (e.g., by comparing with predictions of an optical model) to determine physical parameters of the sample (e.g., of grating-like structures on a silicon wafer) are of particular relevance. Relevant optical instruments may include spectrometry instruments, spectroscopic reflectometers and transmissive spectrophotometers, and especially those spectroscopy instruments, which employ a microscope objective and associated imaging optical components for small-spot viewing of a sample having diffractive features to be measured.

The present invention relates especially to any optical metrology systems characterized by substantially unpolarized sample illumination and by polarization-insensitive detection, so as to allow samples whose optical characteristics strongly depend on polarization (e.g., wafers with gratings) to be measured at arbitrary sample orientations relative to the instrument. The invention also relates to improved depolarizer elements for such instruments.

BACKGROUND ART

Physical properties of a sample can be determined by interpreting measured optical characteristics of the sample. For example, the optical characteristics may describe the light that has scattered from the sample, given the description of the light incident upon the sample. Physical properties of particular interest are parameters of grating-like structures on a silicon wafer. A reflectometer operating at near normal incidence is one example of an optical instrument that can be used to measure the properties of gratings on a wafer. In general, the interpretation mentioned above either implicitly or explicitly compares measured light intensities to the predictions of an optical model, which describes the incident light, the optical characteristics of the sample, and the detection of light.

It is desirable in many situations to allow the wafer to be viewed at any rotational orientation upon its support. Allowance for arbitrary rotation of the sample is desired, for example, if the optical instrument is integrated into a process tool like a lithography track or polishing tool for chemical mechanical polishing. A robot transports wafers (particular samples of interest) within the process tool to various process modules, and also delivers wafers to the metrology system, which contains the optical instrument. The wafer is typically placed on a flat support. The process tool as a whole may not be sensitive to the specific rotation of the wafer at any point, and may have no provision for determining that orientation. Even if the orientation of the wafer is determined at some point in its processing path through the process tool, the process modules or the robot may not maintain this orientation. Since space is typically at a premium in such a process tool, it is preferable to not need an independent "wafer aligner" for the metrology instrument.

The optical characteristics of grating-like structures have a marked sensitivity to the polarization of light. Samples with grating-like structures will affect the amplitude and phase of the light they reflect or transmit differently for different incident polarizations. The same is also true for birefringent samples, or stacks of thin films at other than normal incidence. This can be an issue when making measurements with some photometric instruments. In lithography applications, for example, determining the linewidth or profile of diffractive pattern features formed on a semiconductor wafer or photomask may be performed by measuring the normal or near-normal incidence (hereafter collectively referred to as quasi-normal incidence) reflectivity or other optical properties with a small-spot reflectometer or small-spot transmissive spectrophotometer. The spectral reflectivity or transmissivity of the sample being measured will depend to some extent on the degree of polarization of the incident light and on the orientation of the wafer. Thus, in order to allow arbitrary orientation of a grating sample whose optical characteristics depend strongly on polarization of the light, the illumination by the metrology instrument must be effectively unpolarized. The detection by the instrument must likewise be insensitive to polarization.

In some instruments it is possible to orient the sample so that the grating-like structures of the pattern (or the optical axis of a birefringent surface or thin film stack) are presented in a known and consistent direction relative to the instrument's incident light. Any systematic errors due to polarization can then be minimized during data processing. That is, by carefully characterizing the polarization characteristics of the optics and modeling the effect on a sample's response at a particular sample orientation relative to the polarized light, the measured data can be processed so as to eliminate the polarization effect provided the sample is measured at the modeled orientation.

However, it is not always possible to provide a specified sample orientation to the measuring instrument. Wafer handlers associated with lithography tracks frequently present the samples to the measuring instrument in a consistent but unknown orientation that the measuring instrument itself has no control over. Polishers produce a random sample orientation. Hence, it would be preferable if the instrument's illumination and collection optics were non-polarizing, so that orienting the wafer would be unnecessary.

In the past, the effect of instrument polarization on measurement results have been only a minor issue that has typically been ignored except in those instruments where polarization itself is the parameter being measured. Polarimeters and ellipsometers deliberately use incident light of known polarization. Also, until recently, spectrometry instruments were not used for measuring linewidth, profile, etc. of grating-like structures.

Unwanted polarization in the optics can be caused by polarizing elements such as tilted fold mirrors, beamsplitters, tilted glass surfaces, prisms, and spectrometer gratings. (In this context "polarizing" can mean partially polarizing or in some way affecting the polarization state.) One prior solution has been to reduce the polarization effect of instrument components by carefully arranging the planes of incidence of the tilted components in the system, so that for every such tilted component the instrument also has a similar component tilted in the perpendicular plane to cancel the polarization effect of the first. This use of component pairs requires more room for the optics, so that it cannot be used when a compact system is needed. The pairing technique cannot be used to alleviate the polarization effect in the spectrometer component of the system.

Depolarizers of several types are known. In Zeiss monolithic spectrometers, among others, light is coupled with a fiberoptic bundle that scrambles the polarization. Fiber depolarizers cannot be used in the imaging path because they would also scramble information about the image. Wedge depolarizers, comprising a birefringent wedge plate and an index-matched non-birefringent plate, need to be properly oriented to the polarization of the light to be depolarized. Because they produce a laterally offset double image, they are not well suited for imaging systems.

Figure 1:
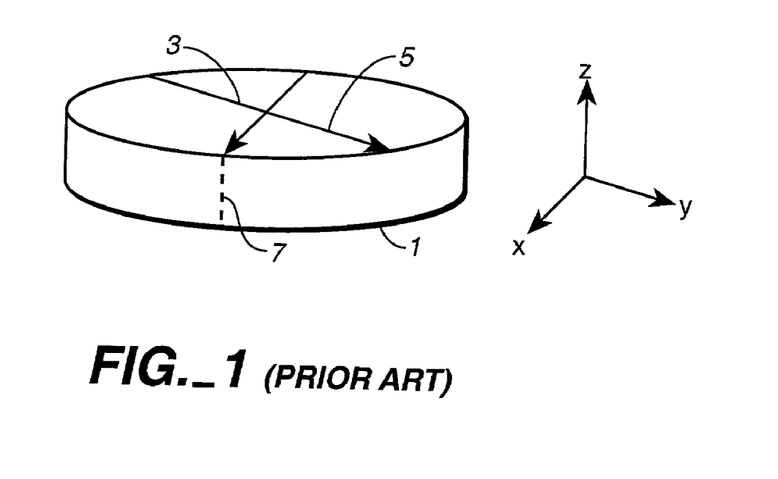
FIG. 1 is a perspective view of a birefringent retardance plate for use in a depolarizer.

Lyot depolarizers, comprising two non-wedge-shaped birefringent plates with their axes at 45° to each other, are commercially available, for example from Karl Lambrecht and other optical component manufacturers. The basic element of a (plate) Lyot depolarizer, as shown in FIG. 1, is a birefringent plate 1 with "retardance" d. The retardance is given by $$d = \frac{2\pi}{\lambda}(n_o - n_e)t = 2\pi k f.$$  Eq. 1 wherein $\lambda$ is the wavelength in vacuum, t is the thickness of the plate, $n_o$ is the optical index of the ordinary axis 3, $n_e$ is the optical index of the extraordinary axis 5, k is the wavenumber (in vacuum), and f is the "retardance frequency": the frequency (i.e., reciprocal period) of oscillations of the optical response of the plate as a function of wavenumber, $$k = \frac{2\pi}{\lambda}$$  Eq. 2

$$f = \frac{(n_o - n_e)t}{2\pi}$$  Eq. 3

(f is not strictly constant with respect to wavelength because $n_o$ and $n_e$ are typically wavelength-dependent, but the wavelength variation of f is typically much smaller than its magnitude.) Fiducial line 7 is for illustrative purposes to indicate the position of the ordinary axis. The frequency of polarization variations induced by the plate is proportional to thickness of the plate and the difference between ordinary and extraordinary indices.

Figure 2:
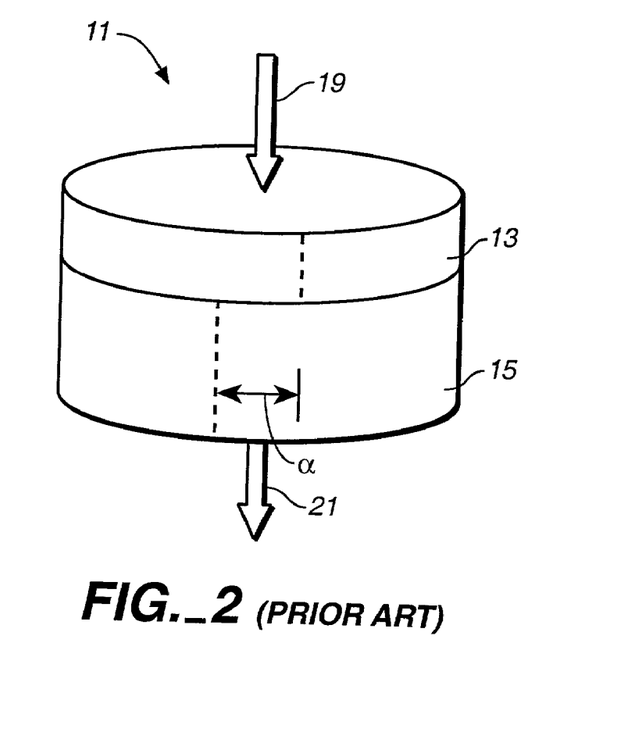
FIG. 2 is a perspective view of a Lyot depolarizer, which uses retardance plates of the type shown in FIG. 1.

As shown in FIG. 2, and described in U.S. Pat. No. 5,371,595, a Lyot depolarizer 11 consists of two birefringent plates 13 and 15 with retardance frequencies in the ratio of 1:2, and with a relative rotation 17 of 45° ($\pi$/4 radians) between their polarization axes. If the two plates are of the same material, the thicknesses will also be in the ratio of 1:2. The thinner plate will have the lower retardance frequency $f_0$ corresponding to retardance d. The thicker will have retardance frequency $2f_0$ corresponding to retardance 2d. The thinner plate is typically about 2 millimeters thick. Incident light 19 passing through the Lyot depolarizer 11 and emerging as transmitted light 21 has its polarization scrambled in a wavelength-dependent manner.

Lyot depolarizers have previously been used in imaging spectroradiometers and spectropolarimeters for telescopes, for example on a satellite observing backscattered radiation from the earth to monitor atmospheric ozone depletion. In contrast to fiber and wedge depolarizers, Lyot depolarizers are image-preserving, and are therefore suitable for imaging systems.

An object of the present invention is to provide a small-spot spectrometry instrument with pattern viewing capability for measuring grating-like or other diffractive pattern structures on semiconductor wafers, photomasks, and the like, wherein the instrument's polarization effects on linewidth, profile, erosion and similar feature measurements are minimized.

Another object of the present invention is to provide a depolarizer that scrambles the polarization as a function of wavelength with improved characteristics, e.g., over a Lyot depolarizer.

An additional object of the present invention is to provide a spectroscopy instrument that behaves as an ideal unpolarized instrument through the use of such an improved depolarizer.

SUMMARY OF THE INVENTION

These objects have been met by a small-spot imaging, spectrometry instrument in which an image-preserving, birefringent retardance plate type, polarization-scrambling element, such as a Lyot depolarizer or an improved three-plate depolarizer, is incorporated between the beamsplitter and the microscope objective. The beamsplitter is the last significant polarizing element in the illumination path prior to the sample. Preferably the polarization-scrambling element is placed in a collimated portion of the light path to avoid creating a double image offset in focus. When both the illuminating and collected light pass through the same depolarizer, there is a preferred orientation for the depolarizer.

The depolarizers used in this invention do not vary the polarization spatially as wedge depolarizers do. Rather, they vary the polarization with wavelength. The sinusoidally perturbed spectrum that results can be removed by data processing techniques. If the depolarizer is made thick enough or made from a highly birefringent material, such as calcite, alpha barium borate or quartz, then the sinusoidal perturbation may be much narrower than the wavelength resolution of the instrument. In this case the perturbation would not be detectable and no processing would be required to remove it. The only disadvantage of using calcite for the depolarizer material is that it does not transmit as much UV light as alpha barium borate or quartz. Disadvantages of alpha barium borate are its high cost, weaker birefringence, and sensitivity to humidity. Quartz has even lower birefringence requiring very thick pieces to make effective depolarizers. The present invention is for an improved depolarizer, which aids in achieving the goal of "unpolarized" illumination and detection in a normal-incidence reflectometer. It allows a sample, even one that changes the state of polarization of light upon reflection, to be measured at an arbitrary rotation.

The second and third objects of the invention have been met through the use of an improved depolarizer that employs at least three birefringent plates. Each birefringent plate has a retardance (i.e., an induced phase shift between two linear polarization modes). The plates are chosen with different retardances, and they assembled with predetermined rotations of their polarization axes with respect to one another and the optical system. In a preferred embodiment, the three depolarizer plates are composed of the same material (e.g., calcite or crystalline quartz) and have a thickness ratio of either 1:3:9 or 4:3:9 (depending on specific design requirements and constraints), although different materials can be used and other thickness ratios can also work. The angles of the outer plates' polarization axes relative to the inner plate's axis are preferably 45° and $[\cos^{-1}(-1/3)]/4=27.368°$.

BEST MODE FOR CARRYING OUT THE INVENTION

Figure 3:
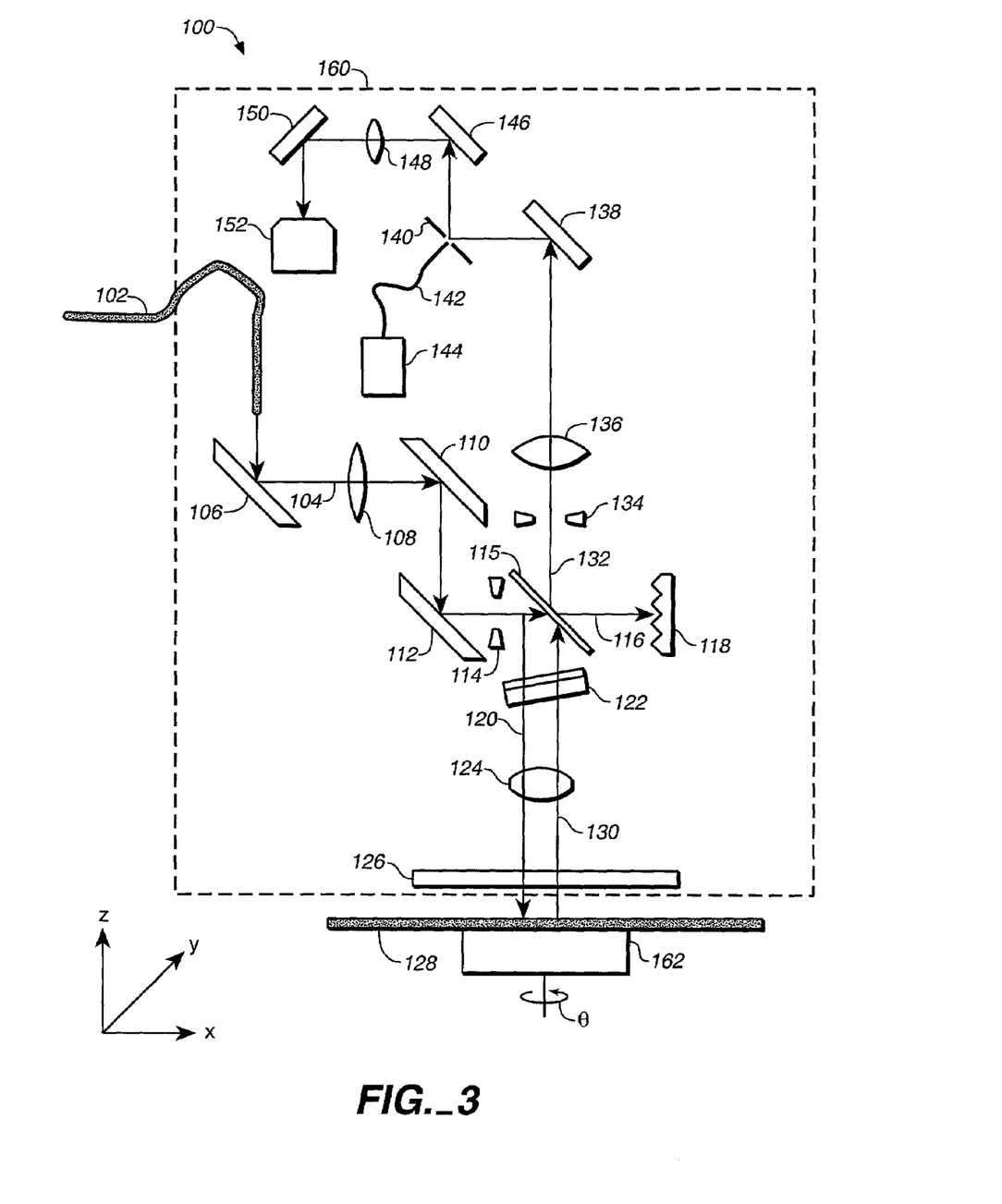
FIG. 3 is a schematic-side plan view of a first embodiment of a spectrometry instrument according to the present invention, with a Lyot depolarizer.

With reference to FIG. 3, a spectrometry instrument 100 in accord with the present invention, to detect reflectivity at a spot of interest on sample 128, is seen to include a Lyot depolarizer 122. The instrument 100 in FIG. 3 is a near-normal incidence reflectometer. Illuminating light beam 104 from a light source (not shown) exits illumination fiber 102. Turn mirror 106 deflects the illuminating light beam 104 through collimator 108. Turn mirrors 110 and 112 direct the light through illumination aperture 114, and on to beam splitter 115. The beam splitter 115 is preferably a plate beam splitter, rather than a cube beamsplitter, to minimize ghost reflections. The beam splitter transmits portion 116 of the illumination beam and beam dump 118 absorbs it. Alternatively, a reference spectrometer could be positioned in place of beam dump 118 to measure the transmitted portion 116. (Or, such a reference spectrometer might be positioned instead to receive light temporarily diverted from path 120 via a flip-in mirror or other beam switch.) Portion 120 of the illumination reflects off beam splitter 115 and propagates through depolarizer 122, objective 124 and window 126, to ultimately illuminate wafer 128.

A window 126 physically isolates the wafer 128 from the metrology instrument 100 and any associated contaminant risk, while still allowing the wafer features to be optically measured. The wafer 128 sits on a support 162 which may be used to move or rotate the wafer under the instrument 100 to one or more specified test positions, as represented by the rotation axis θ. The spectrometry instrument's optics may be mounted to a back plane capable of translating in a lateral direction y relative to the wafer support 162. Focusing motion in a longitudinal direction z may be performed either by moving the objective 124 or sample support 162 or both. A wide area camera system (not shown) might also be provided in addition to CCD camera 152 to locate the general area of interest for measurement by the instrument 100.

Wafer 128 reflects a portion of illumination beam 120 as reflected beam 130, which propagates back to beam splitter 115 via window 126, objective 124 and Lyot depolarizer 122. (For convenience, the illumination and reflected beams 120 and 130 are shown separately in FIG. 3. In practice the beams substantially overlap, although the reflected beam 130 will have different spectral and spatial characteristics.) The portion of reflected beam 130 that is reflected by beamsplitter back towards illumination fiber 106 is ignored. Portion 132 of reflected beam 130 passes through the beam splitter and proceeds through detection aperture 134 and imaging optic 136, via turn mirror 138, to be focused on pin-hole mirror 140. Pin-hole mirror 140 passes a sample of reflected beam 132 through to spectrometer fiber 142 which directs it to spectrometer 144. Pin-hole mirror 140 reflects the remainder of beam 132 back through re-imaging optic 148 to CCD camera 152 via turn mirrors 146 and 150.

Collimator 108 collects the diverging rays exiting illumination fiber 102 as illumination beam 104. The collimator 108 forms an image of the fiber to provide Kohler illumination for the objective 124. Collimator 108, as well as objective 124, imaging optic 136 and re-imaging optic 148 may consist of multiple elements, as is well known in the art. The turn mirrors 110, 112, 138, etc. are for convenience and compactness of packaging. Aperture 114 controls the numerical aperture of beam 120 when it illuminates wafer 128. This is important to prevent vignetting, control the range of incidence angles of light 120 upon wafer 128, as are well known in the art. The depolarizer 122 is preferably oriented at a slight angle to avoid unwanted reflections back along the principal light path. Also, the light between the beamsplitter 115 and the depolarizer 122 is preferably collimated to minimize aberrations. The optics from the illumination source (not shown) through beam splitter can have polarization effects on 120, so that it is typically not unpolarized. Depolarizer 122 will be discussed in some detail below. Objective 124 collects illumination 120 and focuses it on wafer 128, and then collects and collimates reflected light 130. Beam splitter 115 allows illumination beam 120 and reflected beam 130, which is to be detected, to overlap in space. This facilitates behavior as a normal incidence reflectometer. Beam dump 118 is reduces the stray light in the instrument, to improve its accuracy. Detection aperture 134 limits the detection of reflected angles to the detection numerical aperture, may exclude unwanted diffracted orders, and controls the diffraction spot size of the detection system and imaging system, as are well known in the art. Preferably, illumination aperture 114 is larger than detection aperture 134, to produce an overfilled instrument, to limit sensitivity, for example, to tilt of wafer 128. Imaging optic 136 creates an image of the wafer at pin-hole mirror 140. This allows the pinhole to pass a portion of light that has reflected from a well-defined spot on the wafer to be detected by spectrometer 144. The pin-hole mirror reflects the rest of reflected beam 132 (that has not passed through the pinhole) so that re-imaging optic 148 can produce an image of the wafer on CCD camera 152. This image will be missing the spot of light that has passed through pinhole mirror 140 and has been detected by spectrometer 144. This dark spot on the camera image of wafer 128 indicates exact location of the measurement spot with respect to features on the wafer.

Figure 4:
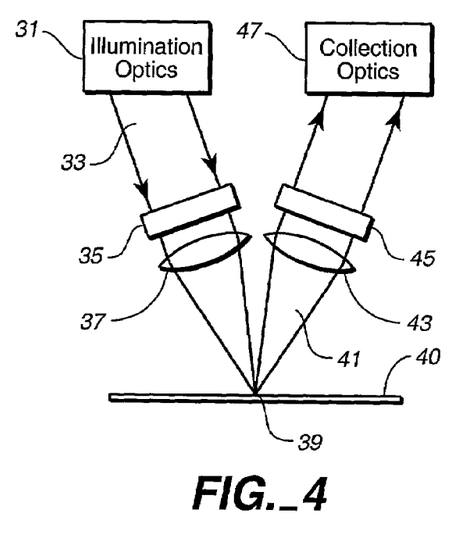
FIGS. 4 and 5 are schematic plan views of two alternate configurations for a spectrometry instrument according to the present invention, one a spectroscopic reflectometer with non-normal incidence and reflection and the other a transmissive spectrophotometer.
Figure 5:
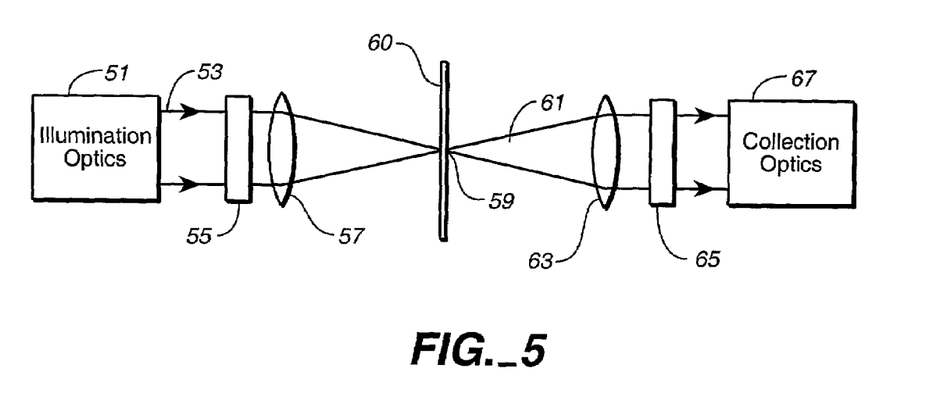

With reference to FIGS. 4 and 5, the spectrometry instrument need not be a normal-incidence reflectometer as in FIG. 3, but could be modified for near normal spectroscopic reflectometry or for transmission spectroscopy. In each case, polarization can be varied with optical frequency by inserting Lyot depolarizers in the light paths. In FIG. 4, a non-normal incidence spectroscopic reflectometer differs from the spectroscopic reflectometer of FIG. 3 by having separate illumination and reflected light paths with a pair of microscopic objectives 37 and 43 and at least one and possibly two depolarizing elements 35 and/or 45. Illumination optics 31, corresponding for example to the optical fiber 102, condensing lens 108 and fold mirrors 106, 110 and 112 in FIG. 3, provide light 33 that is directed through a first Lyot depolarizer 35 and this focused by a microscope objective 37 to a small spot 39 on a sample 40. Light 41 reflected from the sample 40 is gathered by a second microscope objective 43, passed through a second Lyot depolarizer 45 to collection optics 47, corresponding for example to the elements 134–144 in FIG. 3 and including a spectrometer component like element 144 of FIG. 3. In FIG. 5, a transmissive spectrometry instrument for transmission samples 60 also has pairs of depolarizers 55 and 65 and microscope objectives 57 and 63 in separate illumination and collection light paths, which are located on opposite sides of the sample location. Illumination optics 51 provide light 53 whose polarization is varied with wavelength by the Lyot depolarizer 55, which is then focused by a microscope objective 57 to a spot 59 on the sample 60. Light 61 transmitted through the sample 60 is collected by objective 63, again depolarized 65 and sent to collection optics 67 that includes a spectrometer. One or more of the microscope objectives in any of the embodiments could be catadioptric, that is include mirror elements, in which case there may be some advantage to placing the depolarizers between the objective and sample location even though that positioning may increase chromatic aberration. Also, if either the illumination optics 31 or 51 or the collection optics 47 or 67 are such that they do not significantly polarize the light, then the depolarizer 35, 45, 55 or 65 could be removed from that path.

Alternatively, the spectrometer could be replaced with a photodetector and the light source could be a scanning monochromator. In this case, each wavelength band is measured sequentially.

The effect of polarizing elements and depolarizers on light, and ultimately on measurements, is a complex physical phenomenon that may be modeled in a number of different manners. A typical method is the use of Stokes parameters to describe the polarization of light, and Mueller matrices to describe the effect of optical elements on the light. These are described, for example in Chapter 2 of The Handbook of Optics, Vol. 2, 2nd Edition (Michael Bass, editor, 1995). Also see "Ellipsometry and Polarized Light," Azzan and Bashara, 1987.) Light of arbitrary polarization and wavelength is described by the Stokes vector:

$$\begin{pmatrix} S_0 \\ S_1 \\ S_2 \\ S_3 \end{pmatrix} \qquad \text{Eq. 4}$$

$S_0$ is the total intensity of the light, and the $S_1$, $S_2$, and $S_3$ are differences of intensities for different polarizations. Unpolarized light has the Stokes vector $$\begin{pmatrix} S_0 \\ 0 \\ 0 \\ 0 \end{pmatrix}. \qquad \text{Eq. 5}$$

The values of the Stokes vector depend on the orientation of its coordinate system. The coordinate system can be rotated (mathematically) by an angle of p with a rotation Mueller matrix $$R(p) = \begin{bmatrix} 1 & 0 & 0 & 0 \\ 0 & \cos(2p) & -\sin(2p) & 0 \\ 0 & \sin(2p) & \cos(2p) & 0 \\ 0 & 0 & 0 & 1 \end{bmatrix}. \qquad \text{Eq. 6}$$

As noted in the background art section above, the basic element of a (plate) Lyot depolarizer, as shown in FIG. 1, is a birefringent plate 1 with "retardance" d. The retardance is given by $$d = \frac{2\pi}{\lambda}(n_o - n_e)t = 2\pi k f. \qquad \text{Eq. 1}$$

wherein $\lambda$ is the wavelength in vacuum, t is the thickness of the plate, $n_o$ is the optical index of the ordinary axis 3, $n_e$ is the optical index of the extraordinary axis 5, k is the wavenumber (in vacuum), and f is the "retardance frequency": the frequency (i.e., reciprocal period) of oscillations of the optical response of the plate as a function of wavenumber, $$k = \frac{2\pi}{\lambda} \qquad \text{Eq. 2}$$

$$f = \frac{(n_o - n_e)t}{2\pi} \qquad \text{Eq. 3}$$

(f is not strictly constant with respect to wavelength because $n_o$ and $n_e$ are typically wavelength-dependent, but the wavelength variation of f is typically much smaller than its magnitude.) Fiducial line 7 is for illustrative purposes to indicate the position of the ordinary axis. The frequency of polarization variations induced by the plate is proportional to thickness of the plate and the difference between ordinary and extraordinary indices. The Mueller matrix for the plate with its ordinary axis along the x axis is $$D(d) = \begin{pmatrix} 1 & 0 & 0 & 0 \\ 0 & 1 & 0 & 0 \\ 0 & 0 & \cos d & \sin d \\ 0 & 0 & -\sin d & \cos d \end{pmatrix}. \qquad \text{Eq. 7}$$

The Mueller matrix M(p) for a birefringent plate that has been rotated by an angle p is the original (unrotated) Mueller matrix pre- and post-multiplied by two rotation matrices:

$$M(p)=R(p)M(0)R(-p) \qquad \text{Eq. 8}$$

wherein M(0)=D(d), as defined in Eq. 7.

As shown in FIG. 2, a commercially available Lyot depolarizer consists of two birefringent plates 13 and 15 with retardance frequencies in the ratio of 1:2, and with a relative rotation 17 of 45° (π/4 radians) between their polarization axes. The plates 13 and 15 may be composed of any of a variety of available birefringent crystal materials, such as quartz, calcite, or alpha barium borate (BBO). If the two plates are of the same material, the thicknesses will also be in the ratio of 1:2. The thinner plate will have the lower retardance frequency $f_0$ corresponding to retardance d. The thicker will have retardance frequency $2f_0$ corresponding to retardance 2d. The thinner plate is typically about 2 millimeters thick.

Each depolarizer plate material has unique characteristics that should be considered when selecting a depolarizer. Calcite does not transmit as much UV light as alpha barium borate or quartz. Alpha barium borate has weaker birefringence than calcite, is sensitive to humidity, and is expensive. Quartz has even lower birefringence requiring very thick pieces to make effective depolarizers, but transmits UV light very well.

The plates have a retardance that is strongly dependent on wavelength, so this type of depolarizer periodically varies the polarization versus the light's optical frequency. The polarization introduced by the rest of the optics in the metrology instrument then produces a sinusoidal ripple on the measured spectrum. The period of this sinusoidal perturbation is nearly constant in terms of wavenumber, so if the data is averaged over intervals equal to integer multiples of the ripple period, the effect of the sinusoidal variation and thus of the instrument polarization is eliminated. Another way that the sinusoidal ripple effect can be mathematically eliminated during data processing is to regress to find the best-fit theoretical spectrum to the sinusoidally perturbed data assuming an ideal depolarizer. The best theoretical spectrum will naturally follow the middle of the perturbed spectrum. The perturbations may not be evident, and no processing would be required to remove it, if the depolarizer is thick enough and/or made with a highly birefringent material. In that case, the sinusoidal perturbation may be much narrower than the wavelength resolution of the instrument.

A model for a Lyot depolarizer takes incident light 17 having an arbitrary Stokes vector $S_{in}$ (i.e., with an arbitrary state of polarization) and yields the Stokes vector $S_{out}$ for transmitted light 19:

$$S_{out}=R(\pi/4)D(2d)R(-\pi/4)D(d)S_{in} \qquad \text{Eq. 9}$$

$$S_{out} = \begin{bmatrix} S_0 \\ \frac{1}{2}\{+S_12\cos 2d + S_2[\cos d - \cos 3d] - S_3[\sin d + \sin 3d]\} \\ S_2\cos d + S_3\sin d \\ \frac{1}{2}\{+S_12\sin 2d + S_2[\sin d - \sin 3d] - S_3[\cos d + \cos 3d]\} \end{bmatrix}. \qquad \text{Eq. 10}$$

The goal is to have $S_{out}$ unpolarized (Eq. 5). Notice the terms desired to be zero have wavelength-dependent retardances with retardance frequencies of 1, 2 and 3 times the retardance frequency of the thinner of the two plates. If the detection system averages over one or more periods of the lowest retardance frequency the wavenumber-averaged output Stokes vector $<S_{out}>$ is exactly what is desired:

$$\langle S_{out} \rangle = \begin{bmatrix} S_0 \\ 0 \\ 0 \\ 0 \end{bmatrix}, \qquad \text{Eq. 11}$$

i.e., the transmitted light 19 would be effectively depolarized. Typically, a system would not average over an exact integer number of periods of the lowest retardance frequency, but would rather be integrated over some "window" of wavenumbers with a tapered integration weighting function. The spectral width of the weighting function defines the optical system's spectral resolution or "bandwidth". In general, the effective optical response of such a system will tend to approach Eq. 11 as either the system's spectral bandwidth width becomes large or the fundamental retardance frequency $f_0$ becomes large.

The "depolarization" achieved in this way is "effective" depolarization, not true depolarization. In other words, while individual wavenumbers may be at least partially polarized, a "reasonable" average over wavenumber will not be polarized. Assuming that the rapid polarization variations induced by the Lyot depolarizer do not interact in a correlated manner with similar rapid variations induced by other elements in the optical system, the Lyot depolarizer works well.

There are other possible designs for a polarization-scrambling element. For example, more than two plates can be used and different combinations of axes orientation or thickness can be used with nearly the same performance. A single plate can even be used if its optical axis is kept at 45° to the polarizing direction of the sample. Any of these alternative designs can be use in place of, or in combination with, a Lyot depolarizer.

The polarization can also be effectively scrambled by varying the polarization state with time and averaging a detector signal over time. For example, the polarization state can be varied by rotating an optical element between the sample and other polarizing optics, as the signal is detected.

When the illumination and reflected light pass through the same depolarizer as is shown in FIG. 3, some sensitivity to the sample's rotational orientation occurs that varies only slowly with wavelength. This effect can be minimized by orienting the depolarizer so the thin plate is facing the wafer and the optical axis of the thicker plate is parallel to the plane of incidence on beamsplitter 115. This effect can also be minimized by covering part of the aperture of objective 124 with a depolarizer of a different thickness or orientation, but this will degrade the image quality slightly.

However, two Lyot depolarizers in series can lead to problems as the second depolarizer also varies the polarization rapidly. Consider the case of using instrument 100 in FIG. 3 with Lyot depolarizer 122 to detect reflectivity at a spot of interest on sample 128. That the illumination and the reflection from the wafer pass through the same depolarizer is equivalent to using two identical depolarizers in series in a transmission experiment. Depolarizer 122 has several desired functions and properties. It should allow good imaging of the wafer surface on pinhole mirror 140, for good spot size, and onto CCD camera 152. It should allow the wafer to rotate without changing the detected intensity reflected from the spot. In order for this to be true, the light illuminating the wafer should be effectively depolarized, and the light reflected back through the depolarizer should also be effectively depolarized. Since the properties of the rest of the optical system, for example, the beam splitter will cause polarization of the incident light, or polarization sensitivity of the detection, the depolarizer is responsible for effectively depolarizing both the illumination and detection. Finally, the spectrometer signal, the goal of detection, will be compared to some model of optical properties of the wafer and instrument. It is preferable that the optical characteristics of the sample and instrument affecting the spectrometer signal are as easy to model as possible.

The signal response (sig) of an optical system containing an optical subsystem with Mueller matrix M is $$sig = S_D M S_I \quad \text{Eq. 12}$$

wherein $S_I$ is a 4-by-1 Stokes vector that characterizes the illumination source and optics between the source and the subsystem, and $S_D$ is a 1-by-4 "conjugate Stokes vector" that characterizes the optical detector and optics between the subsystem and the detector, $$S_I = \begin{bmatrix} S_{I0} \\ S_{I1} \\ S_{I2} \\ S_{I3} \end{bmatrix}, S_D = [S_{D0} \ S_{D1} \ S_{D2} \ S_{D3}] \quad \text{Eq. 13}$$

For many cases of practical interest the polarization effects of the instrument have a form that is simpler than the most general case of Eq. 12. Typically, the illumination and collection optics have orthogonal linear polarization modes (i.e. polarization states that are unaffected by the optics), in which case the last two components of both $S_I$ and $S_D$ vanish (when referenced to the optical system's natural coordinate frame), $$S_I = \begin{bmatrix} S_{I0} \\ S_{I1} \\ 0 \\ 0 \end{bmatrix}, S_D = [S_{D0} \ S_{D1} \ 0 \ 0] \quad \text{Eq. 14}$$

For an instrument like that shown in FIG. 3 this is expected. (This is the case when the only significantly polarizing elements in the illumination and collection optics are mirrors, and the incidence planes of adjacent mirrors are either parallel or orthogonal.)

For the present discussion, the optical "subsystem" characterized by M comprises the measurement sample 128, depolarizer 122, and any intervening optics (e.g. objective lens 124). Typically, the intervening optics are not significantly polarizing, and their effect be neglected in the following discussion. For many cases of practical interest, the sample has orthogonal linear polarization modes, and its Mueller matrix $M_S$ (referenced to the sample's natural coordinate frame) has the form $$M_s = \begin{bmatrix} R_0 & R_1 & 0 & 0 \\ R_1 & R_0 & 0 & 0 \\ 0 & 0 & R_2 & R_3 \\ 0 & 0 & -R_3 & R_2 \end{bmatrix}. \quad \text{Eq. 15}$$

This must be pre- and post-multiplied by Mueller rotation matrices (Eq. 6) to account for the sample's rotational alignment; thus in the absence of the depolarizer the subsystem Mueller matrix M is $$M = R(p) M_S R(-p). \quad \text{Eq. 16}$$

The detector signal, for no depolarizer, is algebraically $$sig = S_{D0} R_0 S_{I0} + \frac{S_{D1}(R_0 + R_2) S_{I1}}{2} + \quad \text{Eq. 17}$$
$$\cos 2q (S_{D1} S_{I0} + S_{D0} S_{I1}) R_1 + \frac{\cos 4q}{2} S_{D1} S_{I1}(R_0 + R_2)$$

(from Eq's. 6, 12, 14, 15, 16).

With no depolarizer, the detector signal has several undesirable properties. It depends on rotation of the wafer. This either must be accounted for mechanically by ensuring that the wafer is always oriented with respect to optical instrument 100, or mathematically by knowing q and various additional quantities, as shown in the equation. Otherwise, there will be a measurement error introduced by the wafer's rotation. The detector signal depends not only on the wafer's total reflectivity $R_0$, but also on polarization characteristics $R_1$ and $R_2$. Again, to avoid errors, these could be accounted for mathematically, with significant effort. Finally, there are several products of illumination and detection characteristics (the S terms) which must be calibrated or they will cause errors. Calibration means that special samples with known properties are measured on the instrument, and one or more properties of the instrument are determined. Typically these calibration properties of the instrument are stored and used for the interpretation of later measurements.

If the instrument were ideal in the sense that $S_{I1}$ and $S_{D1}$ were zero (in addition to the other zeros implicit in Eq. 14), so that illumination and detection had no polarization, Eq. 17 reduces to $$\text{Sig} = (S_{D0} S_{I0}) R_0 \quad \text{Eq. 18}$$

where there is only one product, $S_{D0} S_{I0}$, that needs to be calibrated, no rotation sensitivity, and only one property of the wafer ($R_0$) to be handled mathematically.

With a Lyot depolarizer, the wafer-depolarizer subsystem described above has a Mueller matrix M given by $$M = D(d) R(\pi/4) D(2d) R(p) M_S R(-p) D(2d) R(-\pi/4) D(d). \quad \text{Eq. 19}$$

(This assumes that the thinner depolarizer plate is furthest from the wafer and is aligned to the instrument's polarization axes. p is the angle between the wafer's and the thicker plate's polarization axes.) The final results of the reflectometer with a Lyot depolarizer and the sample described above is $$sig = S_{D0}R_0S_{I0} + S_{DI}S_{II}\left[\frac{(R_0+R_2)}{4} + \cos 2\frac{d(R_0+3R_2)}{4}\right] - \quad \text{Eq. 20}$$

$$S_{DI}R_3S_{II}\sin 2d\cos 2q - (S_{DI}S_{I0} + S_{D0}S_{II})R_1\cos d\sin 2q +$$

$$\frac{S_{DI}S_{I0}}{4}(-R_0+R_2)(1+\cos d)\cos 4q$$

If the detector effectively integrates over wavelength to cancel out the retardance oscillations of the Lyot depolarizer, the trig functions containing d average out to zero and the resulting spectrally-averaged signal <sig> is $$\langle sig \rangle = S_{D0}R_0S_{I0} + S_{DI}S_{II}\frac{(R_0+R_2)}{4} + \frac{S_{DI}S_{I0}}{4}(-R_0+R_2)\cos 4q \quad \text{Eq. 21}$$

While this result with the Lyot depolarizer and adequate averaging is better than for the instrument with no depolarizer it does not yield the desired result shown in Eq. 18 for an ideal reflectometer. This indicates, as mentioned above, that a Lyot depolarizer operating in double-pass mode does not effectively depolarize light that passes through it, in the manner that a single-pass depolarizer does. A better depolarizer is required to achieve the desired results equivalent to an instrument with no polarization sensitivity.

Figure 6:
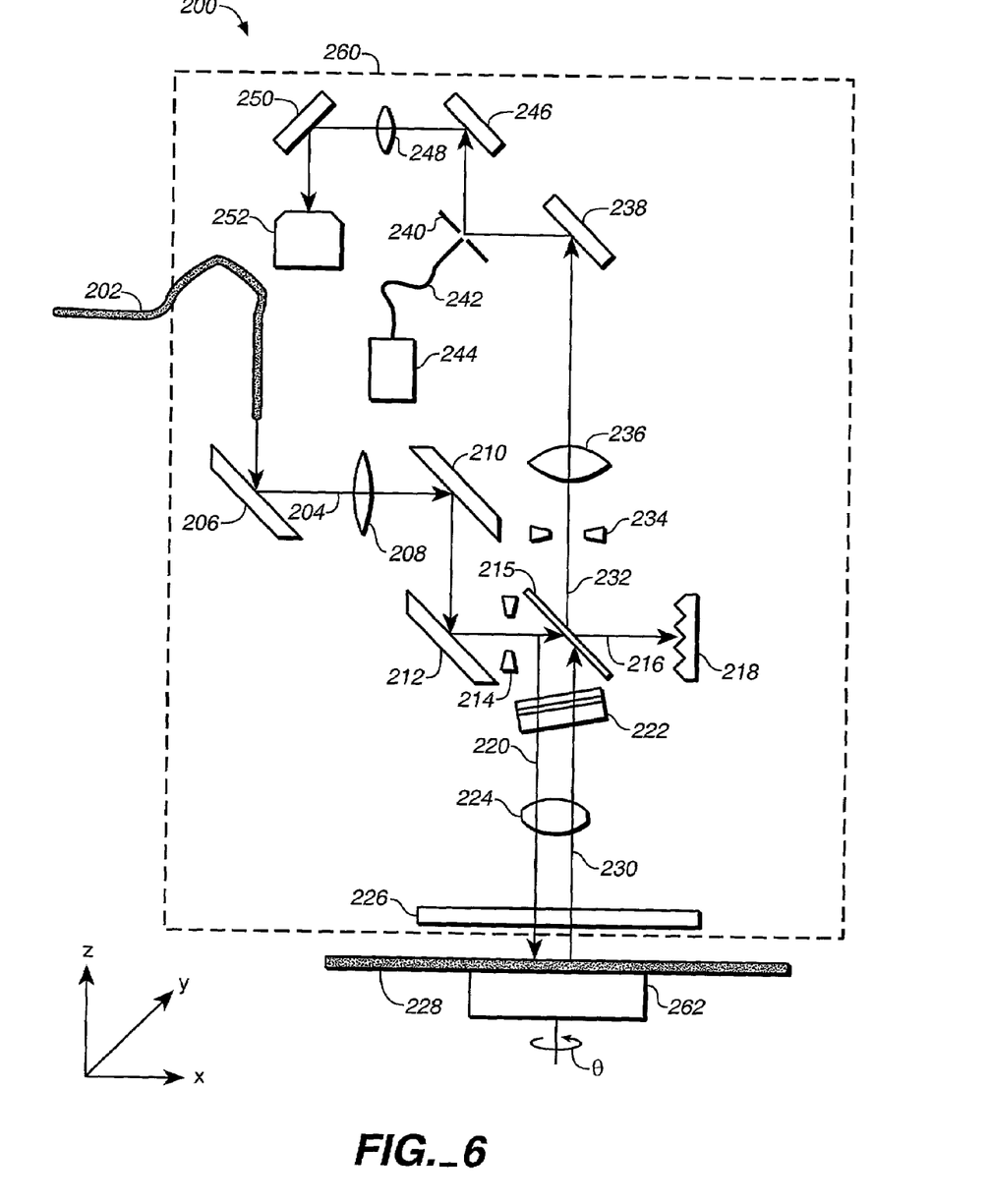
FIG. 6 is a schematic-side plan view of a second spectrometry instrument according to the present invention, with an improved three-plate depolarizer.

FIG. 6 shows a preferred embodiment of the instrument. It is very similar to the prior-art instrument shown in FIG. 3, so only differences and specific preferred aspects will be highlighted here. (Reference numerals in FIG. 6 are incremented by 100 relative to the corresponding elements in FIG. 3.) Again, the preferred light source (not shown) supplies light to fiber 202 with visible and UV light. Like beamsplitter 115, beamsplitter 215 is preferably a plate beamsplitter rather than a cube beamsplitter to avoid ghost reflections and degradation of the cement in UV light. In FIG. 6, the depolarizer 222 preferably consists of three plates with the relations discussed below. Like depolarizer 122, it is preferably oriented at a slight tilt angle to avoid multiple reflections between the depolarizer and the sample. Again, the light between the beamsplitter 215 and depolarizer 222 should preferably be collimated to minimize optical aberrations.

Preferably optics in group 260 are mounted together to allow motion y along a radius of wafer 228, and support 262 allows rotation θ of wafer 228 about the z axis, giving the instrument the capability to scan its spot over the wafer in a polar coordinate system. Focusing motion in a longitudinal (z) direction may be performed either by moving the objective 224 or sample support 262 or both. Many alternative embodiments are possible to allow scanning of the wafer.

Figure 7:
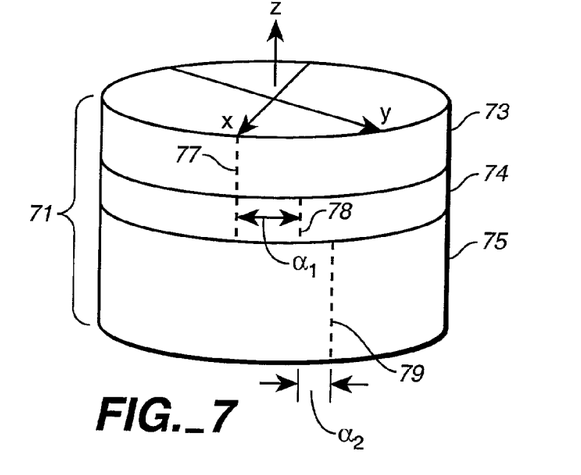
FIG. 7 is a perspective view of a three-plate depolarizer of the present invention for use in a spectrometry instrument as in FIG. 6.
Figure 8:
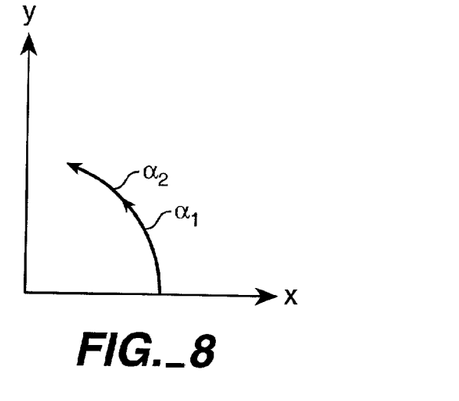
FIG. 8 is a graph illustrating relative polarization axis orientations of the plates 202, 204 and 206 in the depolarizer of FIG. 7, where x and y represent polarization axis directions for plate 202.

A preferred embodiment of a depolarizer is shown in FIG. 7. This depolarizer 71 has three plates 73, 74 and 75, with thicknesses in the ratios of 4:3:9, respectively. (Plate 75 is closest to the wafer.) For example thicknesses of 1.5, 1.125 and 3.375 mm, respectively. The optical axes of the plates are typically parallel to the flat surfaces. Fiducial 77 marks the direction (i.e., the rotation normal to the z axis) of one of the polarization axes of plate 73 (either the ordinary or extraordinary axis). Plate 74 has one of its polarization axes indicated by fiducial 78 and rotated by angle $\alpha_1$ from the polarization axis of plate 73. Angle $\alpha_1$ is preferably equal to 45°, as indicated in FIG. 8. Plate 75 has its polarization axis indicated by fiducial 79, which is rotated by $\alpha_2 \approx 27.3680°$ from the polarization axis of plate 74.

Figure 9:
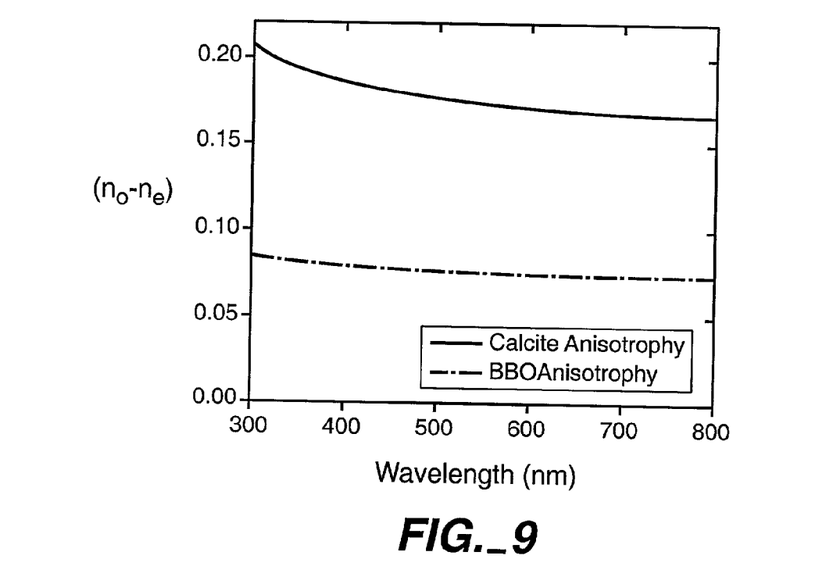
FIG. 9 is a graph of the ordinary-extraordinary refractive index anisotropy ($n_o - n_e$) versus wavelength for calcite and barium borate (BBO) retardance plate materials.

As indicated in the discussion above, the plates in depolarizer 71 are anisotropic with well-defined polarization axes. The preferred depolarizer has plates 73–75 of calcite. The anisotropy of calcite can be characterized as the difference between the ordinary and extraordinary optical indices ($n_o - n_e$), which are themselves functions of wavelength, as shown in FIG. 9. An alternative material is BBO (Barium Borate). It has a lower anisotropy, as shown in FIG. 9, so the plates for equivalent depolarization must be thicker, as discussed below. Another disadvantage is it is hygroscopic, i.e., it absorbs water. One advantage of BBO is lower absorption of especially UV wavelengths.

Generalizing from Eq. 19, the wafer-depolarizer subsystem with the above-described 3-plate depolarizer substituted for the Lyot depolarizer has a Mueller matrix M given by $$M = D(d_1)R(\alpha_1)D(d_2)R(-\alpha_2)D(d_3)\ R(p)M_S\ R(-p) \times D \\ (d_3)R(-\alpha_2)D(d_2)R(-\alpha_1)D(d_1) \quad \text{Eq. 22}$$

wherein $d_1$, $d_2$ and $d_3$ are the retardances of plates 73, 74 and 75, respectively. Upon expanding this expression and applying a trigonometric reduction to the retardance factors, it is evident that Eq. 22 reduces to a linear combination of trigonometric terms of the form $$\cos(m_1d_1+m_2d_2+m_3d_3),\ \sin(m_1d_1+m_2d_2+m_3d_3) \quad \text{Eq. 23}$$

wherein $m_1$, $m_2$ and $m_3$ are integers in the range $$m_1,\ m_2,\ m_3 = 0, \pm 1, \pm 2 \quad \text{Eq. 24}$$

Each such trigonometric argument ($m_1d_1+m_2d_2+m_3d_3$) defines an associated retardance frequency $$f = \frac{(n_o - n_e)}{2\pi}(m_1 t_1 + m_2 t_2 + m_3 t_3) \quad \text{Eq. 25}$$

wherein $t_1$, $t_2$ and $t_3$ are the thicknesses of plates 73, 74 and 75, respectively, cf. Eq. 1. (It is assumed here that the three plates are composed of the same material, which is characterized by ordinary and extraordinary refractive indices $n_o$ and $n_e$.) The smallest such retardance frequency (excluding the trivial case, $m_1=m_2=m_3=0$) defines a "fundamental retardance frequency" $f_0$. Under the assumption that $f_0$ is sufficiently large that polarization variations of this frequency are not resolvable by the instrument, all of the trigonometric functions of retardance (terms of the form indicated in Eq. 23) average out to zero in the spectrally-averaged signal. The resulting signal contains retardance-independent terms that are dependent on the wafer's rotation angle p and polarization properties; however this dependence can be eliminated by choosing appropriate alignment angles $\alpha_1$ and $\alpha_2$ between the plates. The angles that satisfy this criterion are $$a_1 = \frac{\pi}{4} + j_1\frac{\pi}{2} \quad \text{Eq. 26}$$

$$a_2 = \pm\arccos(-1/3)/4 + j_2\frac{\pi}{2} \quad \text{Eq. 27}$$

wherein $j_1$ and $j_2$ are arbitrary integers. For the situation where there is adequate averaging over wavelength, this yields the spectrally-averaged signal <sig>, $$\langle sig \rangle = \left( S_{D0} S_{I0} + \frac{S_{D1} S_{I1}}{3} \right) R_0 \qquad \text{Eq. 28}$$

This is the desired result, as there is no dependence on wafer rotation, one collection of terms $S_{D0}S_{I0}+S_{D1}S_{I1}/3$ which is required for calibration at each wavelength, and only one property of the wafer for calculation, $R_0$. The above result is based on Eq's. 12, 13 and 22—it does not assume the more restrictive form Eq. 14 for $S_I$ and $S_D$. Thus, the operation of the device does not depend on special symmetries of the optical system's polarization properties, and in this mode of operation its performance does not depend on the depolarizer's rotational orientation. Although the above result only applies to a sample having a Mueller matrix $M_S$ having the form of Eq. 15, the result extends partially to the more general case: For an arbitrary sample Mueller matrix $M_S$, <sig> remains insensitive to sample rotation, although it does exhibit some sensitivity to the sample's polarization characteristics.

A key assumption of the above analysis is that the fundamental retardance frequency $f_0$ is sufficiently large that the depolarizer-induced polarization variations are not detectable. The goal is to maximize $f_0$, subject to practical constraints. As an example, consider the case when the response of one pixel of detector 252 has a Gaussian response so its signal output $$<sig>=e\int I(k)\exp[-((k-k_0)/(cw))^2]dk. \qquad \text{Eq. 29}$$

is an integral over wavenumber of the product of the intensity spectrum I(k) and a Gaussian function with a full width, half maximum value of w and center wavenumber $k_0$. c is a constant (~0.6), and e is a constant including the detector efficiency. I(k) is a linear superposition of terms of the form cos(2πf), sin(2πf), with f being a retardance frequency defined by Eq. 25. The integral of Eq. 29 comprises a linear combination of corresponding terms of the form $$v_z = \frac{I_z e}{\sqrt{\pi}\, cw} \exp[-(\pi f cw)^2]. \qquad \text{Eq. 30}$$

Note that the amplitude of such a term decreases rapidly, as a squared inverse exponential, as the retardance frequency f increases, or as the full-width, half-max bandwidth w of the detector increases. The bandwidth of a detector pixel has other requirements placed upon it, for example, it must adequately resolve the sample-induced signal variations with wavenumber. Therefore it is not desirable to make w as wide as might be necessary to obtain good averaging. For a given detector bandwidth, then, it is desirable to have the largest fundamental retardance frequency $f_0$ to resulting from the sums in Eq. 25. The example in Eqs. 29 and 30 assumed a Gaussian form for a detectors response, a common assumption. Similar conclusions would be drawn from other detector response functions.

Increasing the thicknesses of the plates in proportion can always increase the minimum frequency. However, there are other practical limitations on total thickness. One limitation can be absorption in the plates, especially, e.g., in the UV range. Another limitation may be simply size, or cost of the raw material. One solution is to choose the thickness in the ratios of 1:3:9. This is optimal in the sense that, for a given total combined thickness, it yields the highest fundamental frequency $f_0$. A preferred solution may be to choose the thicknesses in the ratios of 4:3:9 so that the thinnest plate is thicker and easier to fabricate and assemble. For the 1:3:9 design $f_0=(n_o-n_e)T/(26\pi)$, wherein T is the total plate thickness ($T=t_1+t_2+t_3$), whereas the 4:3:9 design yields $f_0=(n_o-n_e)T/(32\pi)$.

The performance limitation imposed by the fundamental frequency $f_0$ can be partially circumvented if the optical system satisfies symmetry properties implicit in Eq. 14. For this case, the signal depends only on the four Mueller matrix elements in the first quadrant of M (i.e., the first two rows and columns of M). By choosing the order of the depolarizer plate thicknesses and angles and the orientation of the depolarizer, one or more of the lowest retardance frequencies can be made to vanish in the first quadrant. For both the 1:3:9 and 4:3:9, there are several orderings for which the two lowest frequencies vanish. The 4:3:9 design also has a configuration for which the three lowest frequencies vanish. In this configuration, the thickest plate is in the middle, the thinnest plate is furthest from the wafer, and the angle between the thickest and thinnest plates' polarization axes is 45°. (The polarization axis of the plate furthest from the wafer should be aligned to the instrument's polarization axis.)

As mentioned above, scaling the thicknesses for a given ratio to thicker values gives better averaging properties to achieve effective depolarization, however, it may lead to excessive UV absorption. The preferred thicknesses to balance this tradeoff have a sum of 6 mm: 0.5 mm, 1.125 mm, and 3.375 mm respectively for plates 73, 74 and 75.

Instrument 200, used for illustrative purposes, is a reflectometer. For a true normal-incidence reflectometer, it is necessary to have one depolarizer in the location shown, through which pass both illuminating and detected light. Such an instrument is necessarily implemented with a beam splitter, which typically has polarization effects which need to be removed. However, there are many instruments which have separate illumination and detection "arms" were detection and illumination depolarizers may be placed. For example, a quasi-normal-incidence reflectometer has slight offset illumination and detection beams. Most ellipsometers are other examples. For such instruments, it is sufficient to use two Lyot depolarizers, one in the illumination arm and one in the detection arm, which have thicknesses that allow suitable averaging of the sum and difference frequencies. For example, if the four plates in the two Lyot depolarizers have thickness ratios of 1:2:4:8, i.e., one Lyot depolarizer four times as thick as the other, the lowest frequency will be simply that of the thinnest plate.

Many other embodiments are possible. For example, the plates can be rotated by various angles, or stacked in various orders. While the integer ratio of the thicknesses implied are preferable, other, non-integer ratios are possible. The three plates should preferably be of the same material so that $f_0$ can be simultaneously maximized for all wavelengths (i.e. adjusting the design to increase $f_0$ at one wavelength will not cause $f_0$ to decrease at other wavelengths), but the plates could possibly comprise different materials.

In addition to the use of a depolarizer, other techniques to minimize polarization, particularly in the imaging path, can include component pairing with perpendicular tilt planes and the use of spectrometers with polarization scrambling optical fibers. The depolarizer's main role is in ensuring depolarized illumination of the sample, and to depolarize the diffracted light from the sample before it interacts with any polarization sensitive components in the imaging path of the system.

The invention claimed is:

1. A depolarizer with three birefringent plates having substantially identical birefringent properties, where an angle between polarization axes of two of the plates is substantially $$n\frac{\pi}{2} \pm \arccos(-1/3)/4,$$

where n is an integer.

2. A depolarizer as in claim 1 where the thicknesses of the plates are in the ratio of 1:3:9.

3. A depolarizer as in claim 1 where the thicknesses of the plates are in the ratio of 4:3:9.

4. A depolarizer with three birefringent plates having substantially identical birefringent properties, where a first angle between polarization axes of a first adjacent pair of the plates is substantially $$\left(n+\frac{1}{2}\right)\frac{\pi}{2},$$

and a second angle between polarization axes of a second adjacent pair of the plates is substantially $$n\frac{\pi}{2} \pm \arccos(-1/3)/4,$$

where n is an integer.

5. A depolarizer as in claim 4 where the thicknesses of the plates are in the ratio of 1:3:9.

6. A depolarizer as in claim 4 where the thicknesses of the plates are in the ratio of 4:3:9.

7. A depolarizer with three birefringent plates having substantially identical birefringent properties, where the thicknesses of the plates are in the ratio of 3:4:9 from the thinnest plate to the thickest plate, where a first angle between polarization axes of a first adjacent pair of the plates is substantially $$\left(n+\frac{1}{2}\right)\frac{\pi}{2},$$

and a second angle between polarization axes of a second adjacent pair of the plates is substantially $$n\frac{\pi}{2} \pm \arccos(-1/3)/4,$$

where n is an integer.

* * * * *